(12) United States Patent
Jones et al.

(10) Patent No.: US 11,331,134 B2
(45) Date of Patent: **\*May 17, 2022**

(54) ORTHOPEDIC DEVICE HOLDER

(71) Applicant: Zimmer, Inc., Warsaw, IN (US)

(72) Inventors: Nolan C. Jones, Warsaw, IN (US); Jeffery A. VanDiepenbos, New Paris, IN (US)

(73) Assignee: Zimmer, Inc., Warsaw, IN (US)

( \* ) Notice: Subject to any disclaimer, the term of this patent is extended or adjusted under 35 U.S.C. 154(b) by 475 days.

This patent is subject to a terminal disclaimer.

(21) Appl. No.: 16/297,898

(22) Filed: Mar. 11, 2019

(65) Prior Publication Data

US 2019/0201068 A1 Jul. 4, 2019

Related U.S. Application Data

(63) Continuation of application No. 14/197,994, filed on Mar. 5, 2014, now Pat. No. 10,271,887.

(60) Provisional application No. 61/829,657, filed on May 31, 2013, provisional application No. 61/801,805, filed on Mar. 15, 2013.

(51) Int. Cl.
*A61B 17/88* (2006.01)
*B25G 1/06* (2006.01)
*A61B 17/00* (2006.01)

(52) U.S. Cl.
CPC .. *A61B 17/8872* (2013.01); *A61B 2017/0046* (2013.01); *B25G 1/063* (2013.01)

(58) Field of Classification Search
CPC ... A61B 17/8872; A61B 17/92; A61B 17/921; A61B 17/1659; A61B 2017/0046; A61B 2017/00464; A61B 2017/00469; A61B 2017/00473; A61B 2017/00477; B25G 1/00; B25G 1/04; B25G 1/06; B25G 1/063; B25G 1/10; B25G 1/102; B25G 1/105; B25G 1/066; B25B 3/00; B25B 5/067; B25B 5/082; B25B 5/101; B25F 1/02
USPC ...... 606/86, 84, 99, 79, 80, 53, 104; 81/489, 81/177.1; 16/110.1; 269/3, 6; 29/255, 29/278

See application file for complete search history.

(56) References Cited

U.S. PATENT DOCUMENTS 3,280,439 A 10/1966 McCarthy
5,308,350 A \* 5/1994 Mikhail ................. A61B 17/02
606/53

(Continued)

OTHER PUBLICATIONS

U.S. Appl. No. 14/197,994, filed Mar. 5, 2014, Orthopedic Device Holder.

(Continued)

*Primary Examiner* — Marcela I. Shirsat
(74) *Attorney, Agent, or Firm* — Schwegman Lundberg & Woessner, P.A.

(57) ABSTRACT

An orthopedic device holder and related kit are disclosed. The orthopedic device holder can include a body portion having a proximal end and a distal end, the body portion defining a bore positioned between the proximal end and the distal end, a plunger portion having a proximal end and a distal end, the plunger portion extending into an opening of the body portion and defining a second bore, and a locking lever that, when activated, is configured to move between a first position and a second position and transition the first bore and the second bore from a locked configuration to an unlocked configuration.

17 Claims, 7 Drawing Sheets

(56) References Cited

U.S. PATENT DOCUMENTS

| | | | |
|---|---|---|---|
| 5,443,471 A | 8/1995 | Swajger | |
| 5,499,986 A | 3/1996 | Dimarco | |
| 5,752,285 A * | 5/1998 | Bendheim | A01B 1/20 |
| | | | 172/378 |
| 5,842,394 A * | 12/1998 | Hwang | B25G 1/063 |
| | | | 81/439 |
| 8,096,213 B2 * | 1/2012 | Miers | B25F 1/02 |
| | | | 81/177.85 |
| 10,271,887 B2 * | 4/2019 | Jones | A61B 17/8872 |
| 2014/0277213 A1 | 9/2014 | Jones et al. | |

OTHER PUBLICATIONS

"U.S. Appl. No. 14/197,994, Advisory Action dated Aug. 2, 2018", 3 pgs.
"U.S. Appl. No. 14/197,994, Corrected Notice of Allowability dated Feb. 21, 2019", 7 pgs.
"U.S. Appl. No. 14/197,994, Final Office Action dated May 16, 2018", 17 pgs.
"U.S. Appl. No. 14/197,994, Non Final Office Action dated Oct. 18, 2017", 15 pgs.
"U.S. Appl. No. 14/197,994, Notice of Allowance dated Dec. 20, 2018", 8 pgs.
"U.S. Appl. No. 14/197,994, Response filed Jan. 18, 2018 to Non Final Office Action dated Oct. 18, 2017", 14 pgs.
"U.S. Appl. No. 14/197,994, Response filed Jul. 12, 2017 to Restriction Requirement dated May 19, 2017", 7 pgs.
"U.S. Appl. No. 14/197,994, Response filed Jul. 13, 2018 to Final Office Action dated Jul. 13, 2018", 14 pgs.
"U.S. Appl. No. 14/197,994, Restriction Requirement dated May 19, 2017", 6 pgs.

\* cited by examiner

FIG. 12

ORTHOPEDIC DEVICE HOLDER

RELATED APPLICATIONS

This application is a continuation of U.S. patent application Ser. No. 14/197,994, which claims the benefit of U.S. Patent Application Ser. No. 61/801,805, filed on Mar. 15, 2013, and also claims the benefit of U.S. Patent Application Ser. No. 61/829,657, filed May 31, 2013, the benefit of priority of each of which is claimed hereby, and each of which are incorporated by reference herein in its entirety.

TECHNICAL FIELD

This patent document pertains generally, but not by way of limitation, to an orthopedic device, tool, or instrument holder including a universal connection.

BACKGROUND

Tools or other instruments can be used by a surgeon to complete a surgical procedure (e.g., an orthopedic procedure). For example, intramedullary rods, drill guides, reamers, and pin and screw drivers can be used during the orthopedic procedure. During the procedure, when different instruments or devices are being used, the surgeon may have to switch between various device holders, which can increase surgery time.

OVERVIEW

The present inventors recognize, among other things, that a two-way quick connection and release configuration for a tool or device can be beneficial. The two-way connection allows the orthopedic device holder to be used in different configurations depending on the type of orthopedic tool being used and the preference of a surgeon. Additionally, a single activation can quickly connect and release the orthopedic tool at each configuration. The orthopedic device holder can be readily used with different orthopedic tools of differing sizes.

To further illustrate the orthopedic device holder disclosed herein, a non-limiting list of examples is provided here:

Example 1 can include subject matter such as an orthopedic device holder. The orthopedic device holder can include a body portion having a proximal end and a distal end, the body portion defining a first bore extending in a direction substantially perpendicular to a longitudinal axis of the body portion, the body portion including at least one opening extending into an interior of the first bore, a plunger portion extending into a channel of the body portion and defining a second bore, the plunger portion including at least one opening extending into an interior of the second bore, a locking bar operably coupled to the body portion and moveable between a first position and a second position, such that in the first position, the locking bar is in a locked configuration with respect to the first bore and in the second position, the locking bar is in an unlocked configuration with respect to the first bore, a locking sleeve slidably mounted on the plunger portion and moveable between a first position and a second position, such that in the first position, the locking sleeve is in a locked configuration with respect to the second bore, and in the second position, the locking sleeve is in an unlocked configuration with respect to the second bore, and a locking lever operably coupled to the body portion and configured to move between a first position and a second position to simultaneously transition the locking sleeve and the locking bar from the respective first positions to the respective second positions.

Example 2 can include, or can optionally be combined with the subject matter of Example 1 to optionally include where the first bore and the second bore have a tri-lobe cross-sectional shape, including three substantially flat surfaces.

Example 3 can include, or can optionally be combined with the subject matter of Example 1 or 2 to optionally include where the three substantially flat surfaces are positioned equidistant from each other, each of the three substantially flat surfaces configured to engage with three substantially flat surfaces disposed on an engagement end of an orthopedic device.

Example 4 can include, or can optionally be combined with the subject matter of one or any combination of Examples 1 through 3 to optionally include where the at least one opening extending into an interior of the first bore extends through one of the substantially flat surface of the first bore.

Example 5 can include, or can optionally be combined with the subject matter of one or any combination of Examples 1 through 4 to optionally include where the at least one opening extending into an interior of the second bore extends through one of the substantially flat surfaces of the second bore.

Example 6 can include, or can optionally be combined with the subject matter of Examples 1 through 5 to optionally include where the first bore is substantially perpendicular to the second bore.

Example 7 can include, or can optionally be combined with the subject matter of Examples 1 through 6 to optionally include where the locking sleeve includes at least one locking ball, the at least one locking ball, when the locking sleeve is in the first position, configured to extend at least partially through the at least one opening in the plunger portion and into a mating recess of an orthopedic device.

Example 8 can include, or can optionally be combined with the subject matter of Examples 1 through 7 to optionally include where the locking sleeve, when in the first position, is configured to provide rotational constraint and axial constraint of the orthopedic device.

Example 9 can include, or can optionally be combined with the subject matter of Examples 1 through 8 to optionally include where the locking bar includes at least one locking ball, the at least one locking ball, when the locking bar is in the first position, configured to extend at least partially through the at least one opening in the body portion and into a mating recess of an orthopedic device.

Example 10 can include, or can optionally be combined with the subject matter of Examples 1 through 9 to optionally include where the locking bar, when in the first position, is configured to provide rotational constraint and axial constraint of the orthopedic device.

Example 11 can include, or can optionally be combined with the subject matter of Examples 1 through 10 to optionally include a resilient member positioned around a proximal end of the plunger portion and between the locking sleeve and an interior ledge of the body portion.

Example 12 can include, or can optionally be combined with the subject matter of Examples 1 through 11 to optionally include where the resilient member, when the locking member is in the first position, is in an expanded state.

Example 13 can include, or can optionally be combined with the subject matter of Examples 1 through 12 where the resilient member, when the locking member is in the second position, is in a compressed state.

Example 14 can include subject matter including an orthopedic device holder. The orthopedic device holder can include a body portion having a proximal end and a distal end, the body portion defining a bore positioned between the proximal end and the distal end, a plunger portion extending into a channel of the body portion and defining a second bore, a locking bar operably coupled to the body portion and moveable between a locked position and an unlocked position associated with the first bore, a locking sleeve slidably mounted on the plunger portion and moveable between a locked position and an unlocked position associated with the second bore, and a locking lever operably coupled to the body portion and configured to move the locking bar and the locking sleeve between the respective locked and unlocked positions.

Example 15 can include, or can optionally be combined with the subject matter of Examples 1 through 14 to optionally include where the first bore and the second bore have a tri-lobe cross-sectional shape, including three substantially flat surfaces.

Example 16 can include subject matter including an orthopedic kit. The orthopedic kit can include the orthopedic device holder of claim 1, and at least one orthopedic device including an engagement end having a tri-lobe cross-sectional shape and a circumferential recess sized and shaped to receive a portion of at least one of the locking bar and the locking sleeve.

Example 17 can include, or can optionally be combined with the subject matter of Examples 1 through 16 to optionally include where the at least one orthopedic device includes a plurality of orthopedic devices selected from the group comprising a tibia intramedullary nail, a patella drill guide, a reamer, and a screw driver.

These and other examples and features of the present orthopedic device holders and kits will be set forth in part in the following Detailed Description. This Overview is intended to provide non-limiting examples of the present subject matter—it is not intended to provide an exclusive or exhaustive explanation. The Detailed Description below is included to provide further information about the present orthopedic device holder, kit, and method.

BRIEF DESCRIPTION OF THE DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

DETAILED DESCRIPTION

The present orthopedic device holder (hereinafter referred to interchangeably as "device holder") is configured to provide a quick and easy releasable connection for a plurality of orthopedic devices. The device holder can include a two-way connection such that the operator can select which connection configuration to use. The orthopedic device holder can also prove useful in applications to provide a securable, releasable connection for a plurality of different orthopedic devices used during an orthopedic procedure. The orthopedic device holder and its components can be made of a wide variety of materials, such as metal alloys, stainless steels, aluminum, titanium, polymers, or carbon fiber.

Figure 1:
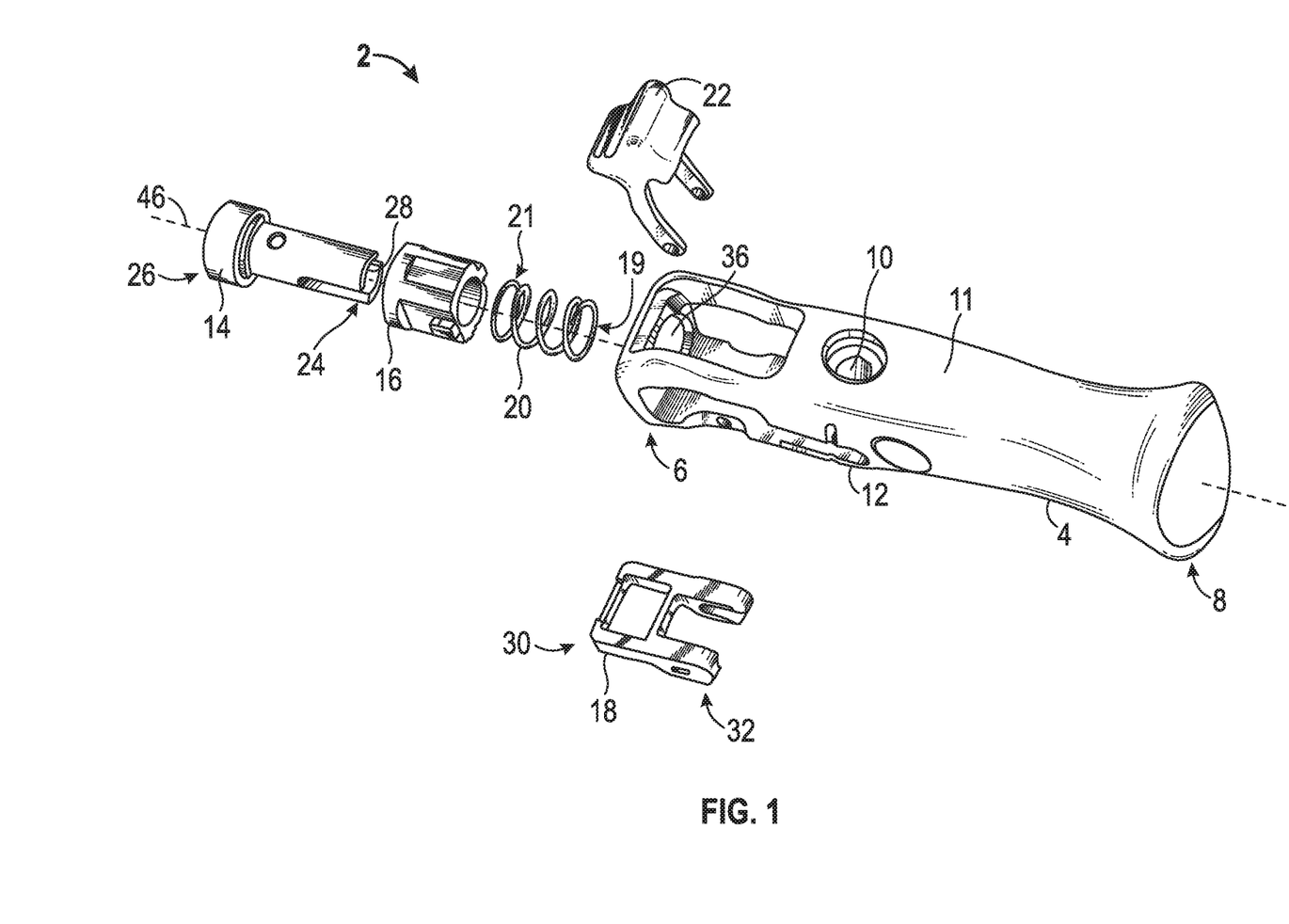
FIG. 1 illustrates an exploded view of an orthopedic device holder, as constructed in accordance with at least one embodiment.

FIG. 1 illustrates an exploded view of an orthopedic device holder 2. The device holder 2 can include a body portion 4, a plunger portion 14, a locking sleeve 16, a locking bar 18, a resilient member 20, and a locking lever 22. The body portion 4 can include a proximal end 8 and a distal end 6. The body portion 4 can define a first bore 10 extending in a direction that is substantially perpendicular to a longitudinal axis 46 of the body portion 4. In an example, the first bore 10 can extend in a direction that forms an oblique angle relative to the longitudinal axis 46 of the body portion 4. In an example, the first bore 10 can extend from a first surface 11 of the body portion 4 to a second surface 12 of the body portion 4. In another example, the first bore 10 can extend through a portion of the body portion 4.

The plunger portion 14 can include a proximal end 24 and a distal end 26. As discussed herein, the plunger portion 14 can extend into a channel 36 of the body portion 4. The plunger portion 14 can define a second bore 28 of the body portion 4. As discussed herein, the first bore 10 and the second bore 28 have substantially identical cross-section geometries such that an orthopedic device can be interchangeably coupled to either the first bore 10 or the second bore 28.

The locking sleeve 16 can be slidably mounted on the plunger portion 14 and can be moveable between a first position and a second position. When the locking sleeve 16 is in the first position, the locking sleeve 16 can be in a locked configuration with respect to the second bore 28. When the locking sleeve 16 is in the second position, the locking sleeve 16 can be in an unlocked configuration with respect to the second bore 28.

The locking bar 18 can include a proximal end 32 and a distal end 30. In an example, the locking bar 18 can be operably coupled to the body portion 4. The locking bar 18 can be moveable between a first position and a second position. When the locking bar 18 is in the first position, the locking bar 18 can be in a locked configuration with respect to the first bore 10. When the locking bar 18 is in the second position, the locking bar 18 can be in an unlocked configuration with respect to the first bore 10.

The locking lever 22 can be operably coupled to the body portion 4. The locking lever 22 can operate as the single activation mechanism that connects and releases an orthopedic tool at each connection point (e.g., the first bore 10 and the second bore 28) of the device holder 2. The locking lever 22 can be configured to move between a first position and a second position. When the locking lever 22 moves from the first position to the second position (e.g., by a user pressing on the locking lever 22), the locking lever 22 can simultaneously transition the locking bar 18 and the locking sleeve 16 from the respective first positions to the respective second positions. Thus, a single activation can transition the orthopedic device holder 2 from a locked configuration to an unlocked configuration at each connection point.

The resilient member 20 can include a proximal end 19 and a distal end 21. The resilient member 20 can be positioned around the proximal end 24 of the plunger portion 14. Additionally, the resilient member 20 can be positioned between the locking sleeve 16 and an interior ledge 38 (as shown in FIG. 2B) of the body portion 4. When the locking lever 22 is in the first position, the resilient member 20 can be in an expanded state. Additionally, when the locking lever 22 is in the second position, the resilient member 20 can be in a compressed state such that when, for example, a user releases the locking lever 22, the locking lever 22 will transition from the second position to the first position due to the force stored in the compressed resilient member 20. As the locking lever 22 transitions from the second position to the first position, the locking sleeve 16 and the locking bar 18 can also transition from the respective second positions to the respective first positions.

Figure 2A:
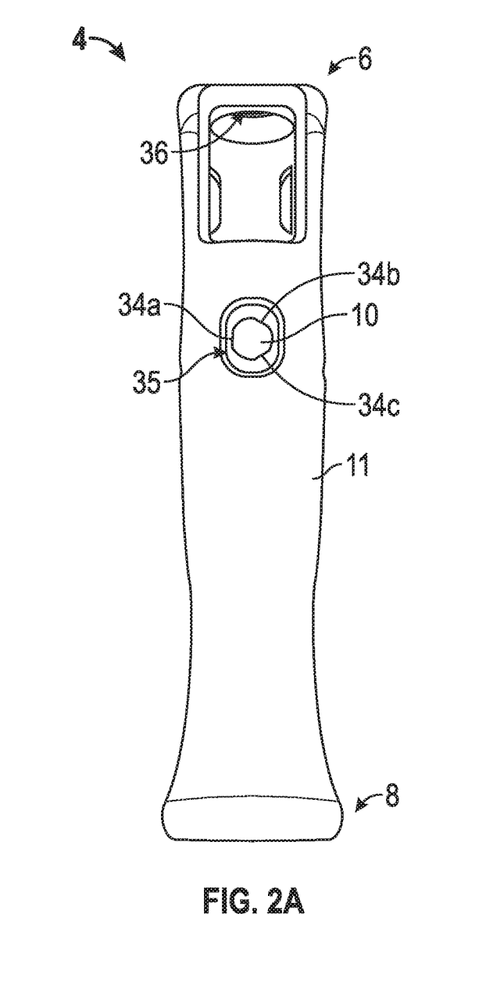
FIG. 2A illustrates a back view of a body portion, as constructed in accordance with at least one example.
Figure 2B:
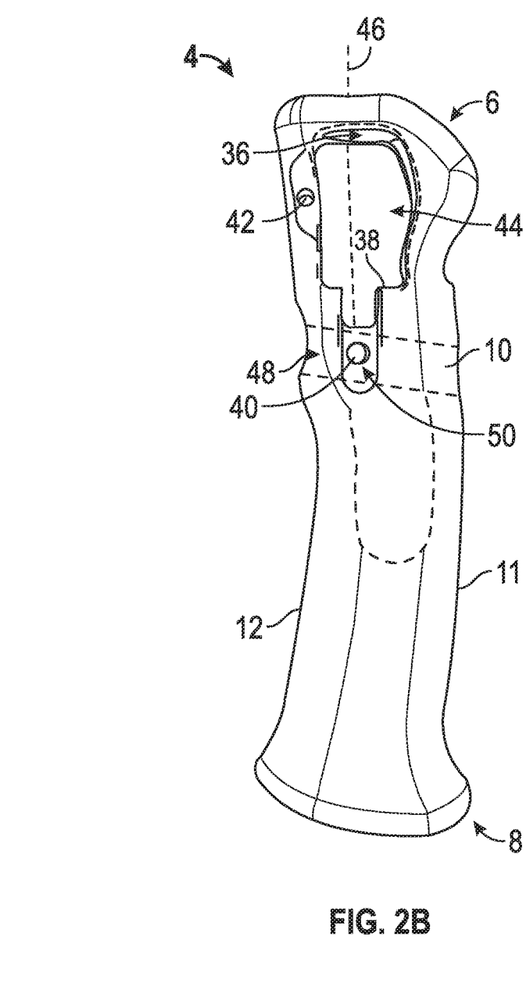
FIG. 2B illustrates a side view of the body portion in FIG. 2A.

FIG. 2A illustrates a rear view of a body portion 4, as constructed in accordance with at least one example. As illustrated in the example of FIG. 2A, the first bore 10 has a tri-lobe cross-sectional shape. That is, the first bore 10 includes three substantially flat surfaces 34A-34C (collectively referred to as "substantially flat surfaces 34"). In an example, the substantially flat surfaces 34 can be positioned equidistant from each other. In an example, the body portion 4 can include a counter-bore 35 having a diameter larger than the diameter of the first bore 10.

Figure 8:
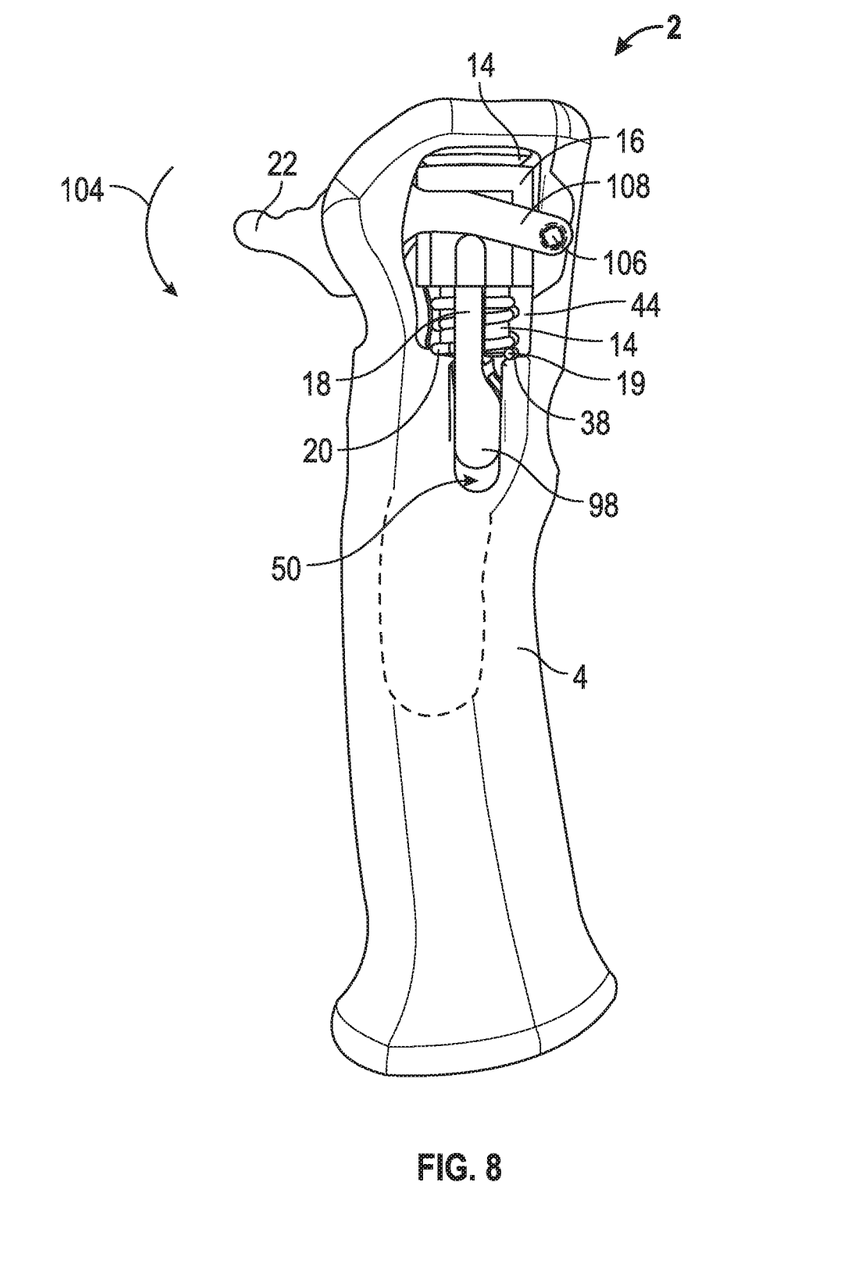
FIG. 8 illustrates an assembled orthopedic device holder, as constructed in accordance with at least one example.

FIG. 2B illustrates a side view of the body portion 4 in FIG. 2A. As illustrated in FIG. 2B, the first bore 10 can extend from the first surface 11 to the second surface 12. In an example, the first bore 10 can be substantially perpendicular to a longitudinal axis 46 of the body portion 4. In another example, the first bore 10 can form an oblique angle relative to the longitudinal axis 46. The body portion 4 can define a channel 36 that can receive the proximal end 24 of the plunger portion 14 (as shown in FIG. 1). The body portion 4 can define a space 44 that can receive, when assembled, at least a portion of the plunger portion 14, the locking sleeve 16, the locking bar 18, and the resilient member 20 (as shown in FIG. 8). The space 44 can define a ledge 38 that can engage with the resilient member 20 (as shown in FIG. 8).

The body portion 4 can include at least one opening 40 in a side wall of the first bore 10. The at least one opening 40 can be configured such that it extends into an interior 48 of the first bore 10. In an example, the body portion 4 can include two openings 40 extending into the interior 48 of the first bore 10. In still another example, the body portion 4 can include more than two openings 40 extending into the interior 48 of the first bore 10. The body portion 4 can also define an indentation 50. As described herein, the indentation 50 can interact with the locking bar 18 as the locking lever 22 is transitioned from the first position to the second position. The body portion 4 can also define a locking hole 42 that can receive a locking bar 106 to lock the locking lever 22 to the body portion 4 (as shown in FIG. 8).

Figure 3A:
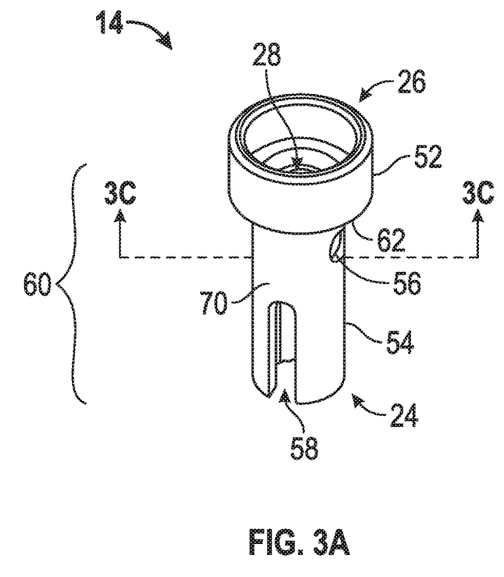
FIG. 3A illustrates a perspective view of a plunger portion, as constructed in accordance with at least one embodiment.
Figure 3B:
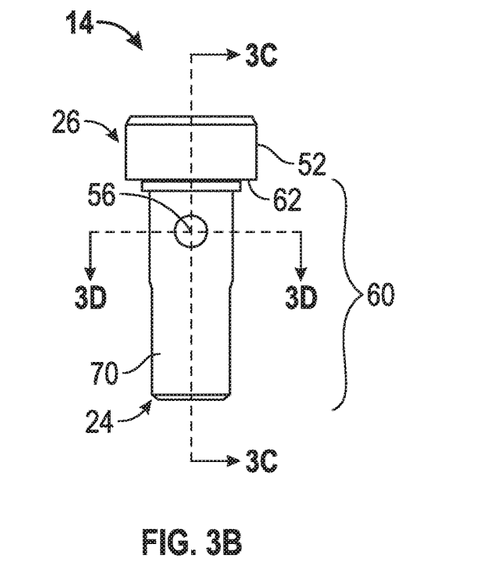
FIG. 3B illustrates a side view of the plunger portion in FIG. 3A.

FIG. 3A illustrates a perspective view of the plunger portion 14, as constructed in accordance with at least one example. FIG. 3B illustrates a side view of the plunger portion 14 in FIG. 3A. The distal end 26 of the plunger portion 14 can include a head portion 52 that is configured to couple with the channel 36 (as shown in FIG. 2B) in the body portion 4. For example, the head portion 52 can define a protuberance 62 that can engage with a protuberance within the channel 36 of the body portion 4. The plunger portion 14 can also include an elongate body portion 60 that can define the second bore 28. The plunger portion 14 can also include at least one opening 56 extending into an interior 72 (shown in FIG. 3C) of the second bore 28. For example, the opening 56 can extend from an exterior surface 70 of the plunger portion 14 to the interior surface 72 (shown in FIG. 3C). In an example, the plunger portion 14 can include two openings 56. In another example, the plunger portion 14 can include more than two openings 56. As illustrated in FIG. 3A, the elongate body portion 60 can further define a longitudinally extending slot 58. In an example, the elongate body portion 60 can include two longitudinally extending slots 58 that are diametrically opposed from one another. As described herein, the longitudinally extending slot 58 can receive a portion of the locking bar 18 such that the locking bar 18 can move in a direction along the longitudinally extending slot 58.

Figure 3C:
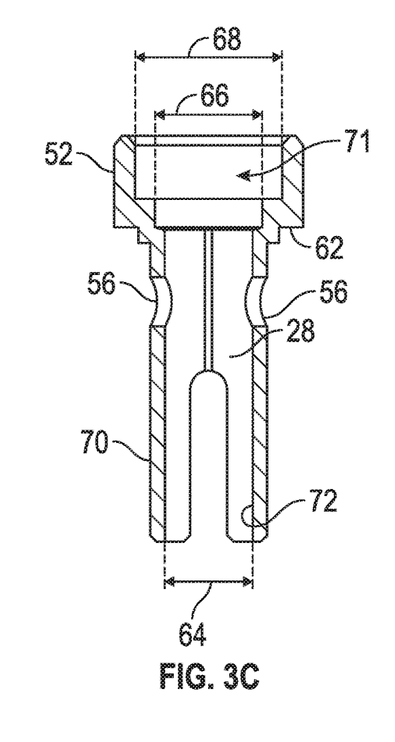
FIG. 3C illustrates a partial cross-section view of the plunger portion in FIG. 3B along lines 3C-3C.

FIG. 3C illustrates a cross-section of the plunger portion 14 in FIG. 3B along lines 3C-3C. As illustrated in FIG. 3C, the plunger portion 14 can define two openings 56 that extend from the exterior surface 70 to the interior surface 72. The second bore 28 can have a diameter 64 from about 7.0 millimeters to about 7.5 millimeters. In some examples, the head portion 52 can define an opening 71 that includes include one or more diameters (e.g., diameter 66 and diameter 68). In an example, diameters 66, 68 can be different from the diameter 64 of the second bore 28. In an example, diameters 64, 66, and 68 are different from each other. In another example, the diameters 66, 68 can be equal to each other but different from diameter 64. In still another example, diameters 64, 66, and 68 can be substantially equal.

Figure 3D:
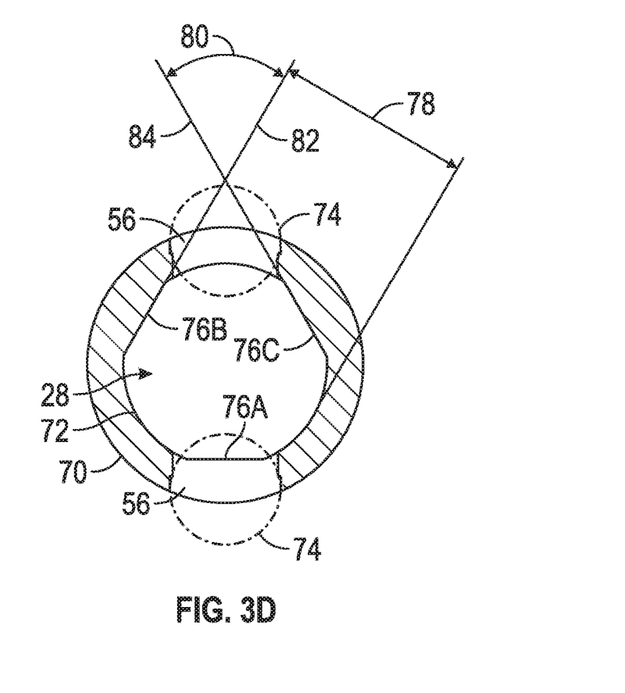
FIG. 3D illustrates a cross-section view of the plunger portion in FIG. 3B along lines 3D-3D.

FIG. 3D illustrates a cross-section view of the plunger portion 14 in FIG. 3B along lines 3D-3D. As illustrated in FIG. 3D, the second bore 28 includes three substantially flat surfaces 76A-C (collectively referred to as "substantially flat surfaces 76"). The substantially flat surfaces 76 can be positioned equidistant from each other. In an example, between adjacent substantially flat surfaces 76A-C can be a curved surface. For example, the curved surface can be a concave surface. In an example, a length of each one of the substantially flat surfaces 76 can be substantially equal. In an example, an angle 80 formed by lines 82, 84 that are tangent to two adjacent substantially flat surfaces 76 (e.g., flat surface 76B and flat surface 76C) can be about 60 degrees. In an example, a diameter 78 extending from a substantially flat surfaces (e.g., substantially flat surface 76B) to a midpoint of a curved surface (e.g., surface between substantially flat surface 76C and 76A) can be from about 7.0 millimeters to about 7.5 millimeters. In an example, one of the substantially flat surfaces 76 can be aligned with one of the openings 56 of the plunger portion 14. For example, substantially flat surface 76A can be aligned with one of the openings 56.

As illustrated in FIG. 3D, locking balls 74 can be shaped and sized such that a portion of the locking ball 74 can extend into the second bore 28 when the locking lever 22 (as shown in FIG. 1) is in the first position. The substantially flat surfaces 76 can be configured to engage with corresponding substantially flat surfaces of an orthopedic device that is positioned within the second bore 28. The engagement of the substantially flat surfaces 76 of the second bore 28 and the substantially flat surfaces of the orthopedic device can allow for rotational constraint. That is, as rotational motion is applied to the body portion 4, the body portion 4, as well as an orthopedic device positioned within the second bore 28, will rotate together. As discussed herein, the locking balls 74 can be configured to extend through the at least one opening 56 in the plunger portion 14 and fit into a mating recess of an orthopedic device. The engagement of the locking balls 74 and the mating recess allow for axial constraint of the orthopedic device. That is, as force is applied along the longitudinal axis (e.g., pushing or pulling), the orthopedic device can move simultaneously with the orthopedic device holder 2. Thus, the orthopedic device holder 2 can allow for rotational and axial constraint of an orthopedic device positioned within the second bore 28. While FIG. 3D is discussed with reference to the second bore 28, the first bore 10 can have the same dimensions such that an orthopedic device can be coupled to either the first bore 10 or the second bore 28.

Figure 4A:
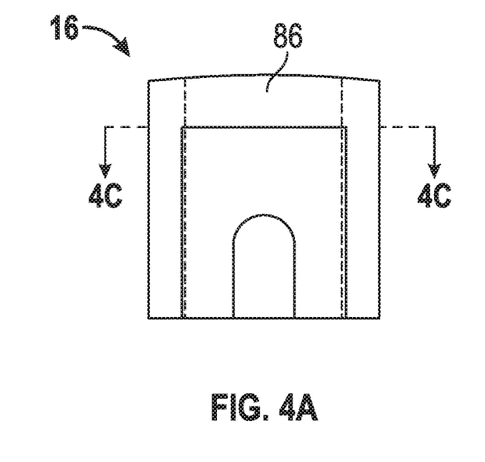
FIG. 4A illustrates a side view of a locking sleeve, as constructed in accordance with at least one embodiment.
Figure 4B:
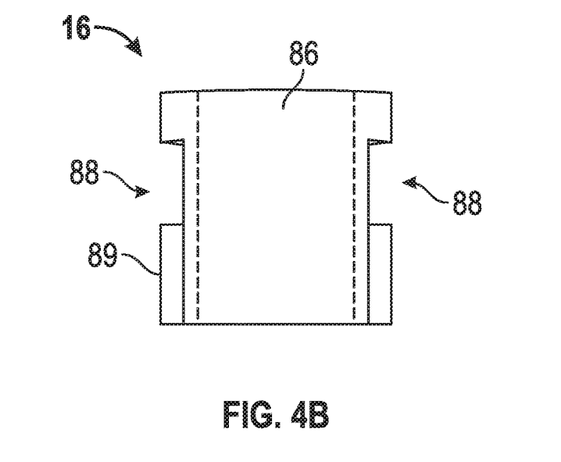
FIG. 4B illustrates a front view of the locking sleeve in FIG. 4A.

FIG. 4A illustrates a side view of a locking sleeve 16, as constructed in accordance with at least one example. FIG. 4B illustrates a front view of the locking sleeve 16 in FIG. 4A. The locking sleeve 16 can be part of a locking mechanism that can be configured to couple an orthopedic instrument within the second bore 28 (as shown in FIG. 3A-3C). The locking mechanism for the second bore 28 can include the locking sleeve 16 and two locking balls 74 (as shown in FIG. 3D). The locking sleeve 16 can include a channel 86 configured to receive the elongate body portion 60 (as shown in FIGS. 3A-3C) of the plunger portion 14. As illustrated in FIG. 4B, the external surface 89 of the locking sleeve 16 can define one or more grooves 88. The one or more grooves 88 can engage with locking arms 108 of the locking lever 22 (as shown in FIG. 8). The engagement between the locking arms 108 and the locking lever 22 can enable the locking sleeve 16 and the locking bar 18 to move between the first position and the second position when the locking lever 22 is actuated, as discussed herein.

Figure 4C:
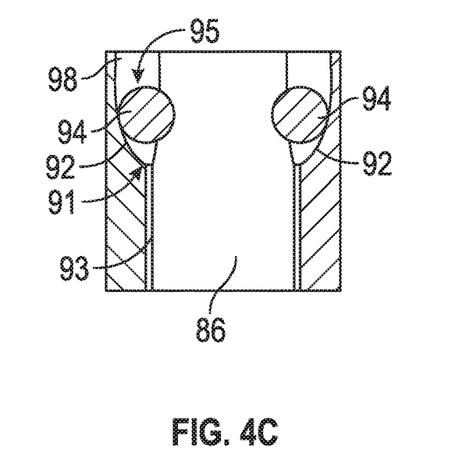
FIG. 4C illustrates a cross-section view of the locking sleeve in FIG. 4A along lines 4A-4A.

FIG. 4C illustrates a cross-section view of the locking sleeve 16 in FIG. 4A along lines 4C-4C. The locking sleeve 16 can include one or more locking balls 94 configured to engage with the one or more openings 56 (illustrated in FIG. 3A-3C) of the plunger portion 14. In an example, the internal surface 93 of the locking sleeve 16 that defines the channel 86 can include at least one ramped surface 92. In the example illustrated in FIG. 4C, the locking sleeve 16 includes two ramped surfaces 92 and two locking balls 94.

The ramped surfaces 92 can be positioned, when assembled, near the opening 56 in the plunger portion 14.

While the locking lever 22 is in the first position, the locking balls 94 can be positioned near a first end 91 of the ramped surface 92 and partially extend through the opening 56 in the plunger portion 14 and can fit into a mating recess of an orthopedic device. The engagement between the locking balls 94 and the mating recess of the orthopedic device can prevent axial movement of the orthopedic device. The ramped surfaces 92 can interact with the locking balls 94 as the locking lever 22 is transitioned from the first position (e.g., locked positioned) to the second position (e.g., unlocked position). For example, as the locking lever 22 transitions form the first position to the second position, the locking sleeve 16 can move relative to the plunger portion 14. As the locking sleeve 16 moves relative to the plunger portion 14, the relationship between the ramped surfaces 92 and the locking balls 94 changes such that the locking balls 94 are substantially positioned within a cavity 95 formed by the ramped surfaces 92. Thus, while the locking lever 22 is in the second position, the locking balls 94 are not positioned within the second bore 28 of the plunger portion 14 and do not engage the orthopedic device positioned within the second bore 28 (as shown in FIG. 3C).

Figure 5:
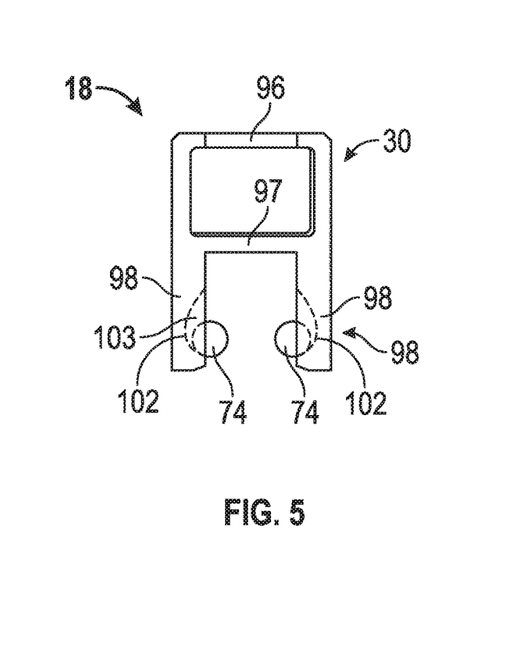
FIG. 5 illustrates a front view of a locking bar, as constructed in accordance with at least one example.

FIG. 5 illustrates a front view of the locking bar 18, as constructed in accordance with at least one example. The locking bar 18 can be part of a locking mechanism configured to couple an orthopedic device within the first bore 10. The locking mechanism can include the locking bar 18 and two locking balls 74. The locking bar 18 can include a distal locking bar 96, a proximal locking bar 97, and two locking arms 98. Each of the two locking arms 98 can include a ramped surface 102 that defines a cavity 103. The ramped surfaces 102 can be positioned, when assembled, near the openings 40 extending into the interior of the first bore 10 such that the ramped surfaces 102 can engage with the locking balls 74. The locking balls 74 can secure the engagement between the first bore 10 and an orthopedic device positioned within the first bore 10. For example, while the locking lever 22 is in the first position, a portion of each locking ball 74 can extend into the first bore 10 and can engage with a mating recess of an orthopedic device positioned within the first bore 10.

Figure 6:
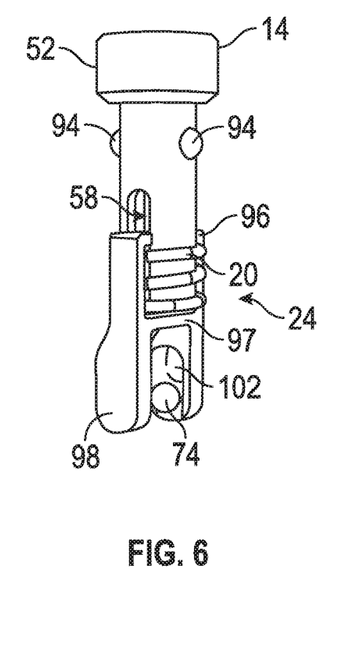
FIG. 6 illustrates a partially assembled orthopedic device holder, as constructed in accordance with at least one example.

FIG. 6 illustrates a partially assembled orthopedic device holder 2 (as shown in FIG. 1), as constructed in accordance with at least one example. As illustrated in FIG. 6, at least the distal locking bar 96 is positioned within and moveable along the longitudinal slot 58 of the plunger portion 14. The resilient member 20 can be positioned around a proximal end 24 of the plunger portion 14. The resilient member 20 can also be positioned between the distal locking bar 96 and the proximal locking bar 97. The proximal end 19 of the resilient member 20 is configured to contact the ledge 38 (as shown in FIG. 8) defined by the body portion 4.

Figure 7:
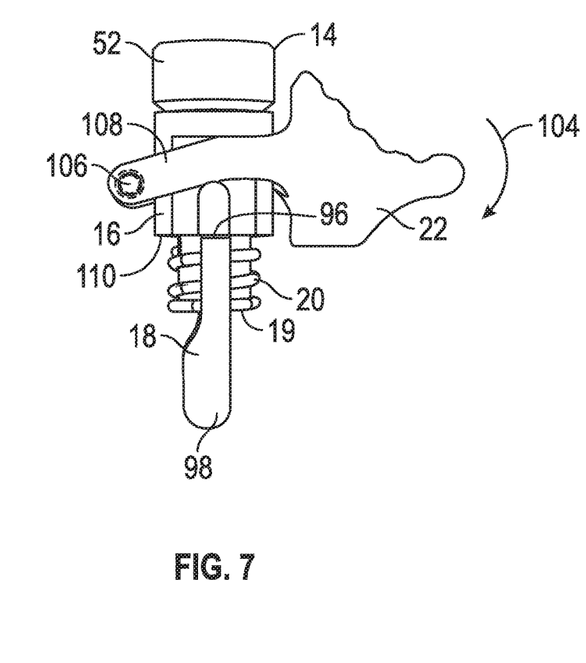
FIG. 7 illustrates a partially assembled orthopedic device holder, as constructed in accordance with at least one example.

FIG. 7 illustrates a partially assembled orthopedic device holder 2 (as shown in FIG. 2), as constructed in accordance with at least one example. As illustrated in FIG. 7, the locking sleeve 16 and the resilient member 20 are positioned around the plunger portion 14. The resilient member 20 can be positioned between the distal locking bar 96 and the proximal locking 97 (as shown in FIG. 6). A proximal end 110 of the locking sleeve 16 can contact the distal locking bar 96 of the locking bar 18. The locking lever 22 includes locking arms 108 that can couple to the body portion 4 via locking bar 106. For example, the locking bar 106 can extend through locking hole 42 (as shown in FIG. 2B) of body portion 4. As illustrated in FIG. 7, the locking arms 108 are positioned within the groove 88 (as shown in FIG. 4B) defined by the locking sleeve 16. While locking lever 22 is in the first position (e.g., a locked configuration), the resilient member 20 is in an expanded state. Additionally, while the locking lever 22 is in the first position, a portion of the locking balls 74 extends into the first bore 10 and a portion of each of the locking balls 94 extends into the second bore 28. As the locking lever 22 is transitioned from the first position (locked configuration) to the second position (unlocked configuration) (e.g., by providing force in the direction of direction arrow 104), the locking arms 108 can move the locking sleeve 16 and the locking bar 18 relative to the plunger portion 14 thereby compressing the resilient member 20.

As the locking sleeve 16 moves relative to the plunger portion 14, the ramped surfaces 92 of the locking sleeve 16 interact with the locking balls 94 such that the locking balls 94 are positioned within the cavity 95 formed by the ramped surfaces 92. In other words, the locking balls 94 are no longer engaging the openings 56 of the plunger portion 14. Similarly, as the locking bar 18 moves relative to the plunger portion 14, the ramped surfaces 102 of the locking bar 18 interact with the locking balls 74 such that the locking balls 74 are positioned within the cavity 103 formed by the ramped surfaces 102. In other words, the locking balls 74 are no longer engaging the openings 48 of the body portion 4.

FIG. 8 illustrates an assembled orthopedic device holder 2, as constructed in accordance with at least one example. The locking lever 22 can be operable coupled to the body portion 4 via the locking arms 108 and the locking bar 106. The locking sleeve 16 and the resilient member 20 can be positioned around plunger portion 14. The resilient member 20 can be positioned between the distal locking bar 96 and the proximal locking bar 97 (as shown in FIG. 6) where the proximal end 19 of the resilient member 20 engages the ledge 38 of the body portion 4. As illustrated in FIG. 8, the orthopedic device holder 2 is in a first position, which is a locked configuration. That is, the locking balls 74 and 94 are partially positioned within the first bore 10 and the second bore 28, respectively. As the locking lever 22 transitions from the first position to the second position (e.g., applying force in the direction of direction arrow 104), the locking arms 108 apply a force (e.g., a downward force) to the locking sleeve 16 and the locking bar 18. The locking sleeve 16 and the locking bar 18 can move relative to the plunger portion 14. As the locking sleeve 16 and the locking bar 18 move relative to the plunger portion 14, the resilient member 20 becomes compressed as the space between the ledge 38 and the distal locking bar 96 decreases.

As the locking lever 22 transitions to the second position, the locking arms 98 can move within the indentations 50 of the body portion 4. As the locking arms 98 move within the indentations 50, the relationship between the ramped surfaces 102 and the locking balls 74 changes such that the locking balls 74 are substantially positioned within a cavity 103 formed by the ramped surfaces 102, as shown in FIGS. 5 and 6. Thus, while the locking lever 22 is in the second position, the locking balls 74 are not positioned within the first bore 10 of the body portion 4.

As the locking lever 22 transitions to the second position, the locking sleeve 16 moves along the plunger portion 14. As the locking sleeve 16 moves along the plunger portion 14, the relationship between the ramped surfaces 92 and the locking balls 94 changes such that the locking balls 94 are substantially poisoned within a cavity 95 formed by the ramped surfaces 92, as shown in FIG. 4C. Thus, while the locking lever 22 is in the second position, the locking balls 94 are not positioned within the first bore 10.

Figure 9:
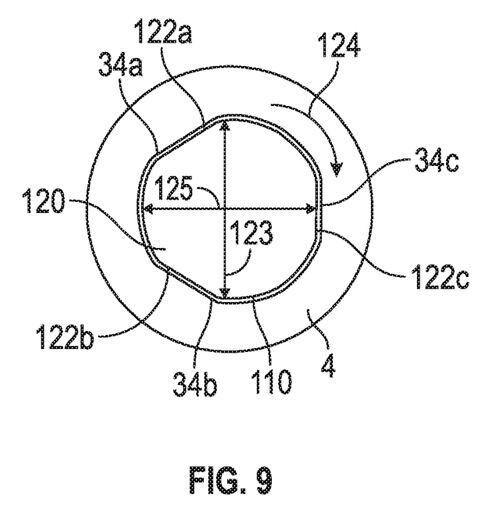
FIG. 9 illustrates an orthopedic device within a bore of the orthopedic device holder, as constructed in accordance with at least one example.

FIG. 9 illustrates an orthopedic device 120 within the first bore 10 of the orthopedic device holder 2, as constructed in accordance with at least one example. In the example illustrated in FIG. 9, the orthopedic device 120 is positioned within the first bore 10 of the body portion 4. The orthopedic device 120 includes a tri-lobe cross-section shape and has three substantially flat surfaces 122A-C that correspond to the three substantially flat surfaces 34A-C of the first bore 10. If a rotational force 124 is applied to the orthopedic device holder 2, the orthopedic device holder 2 and the orthopedic device 120 can rotate together as the edges of the tri-lobe shape of the orthopedic device 120 engage the interior surface of the first bore 10. In an example, diameter 123 can be about 7.0 millimeters to about 7.5 millimeters, while diameter 125 can be about 6.3 millimeters to about 6.8 millimeters. However, other diameters are possible.

Figure 10:
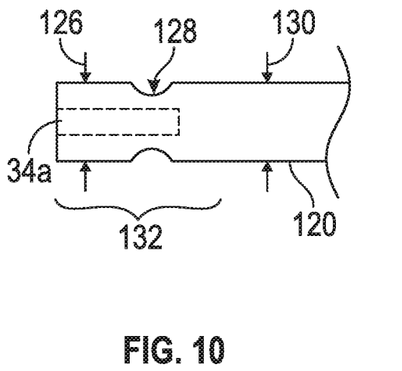
FIGS. 10-12 illustrate various orthopedic devices that can be used with the orthopedic device holder, as constructed in accordance with at least one example.
Figure 11:
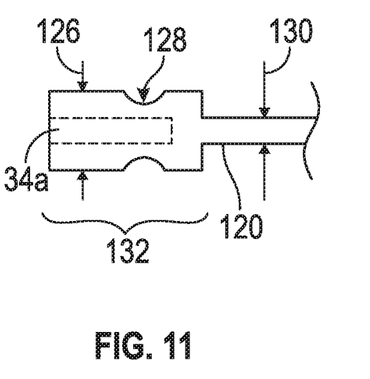
Figure 12:
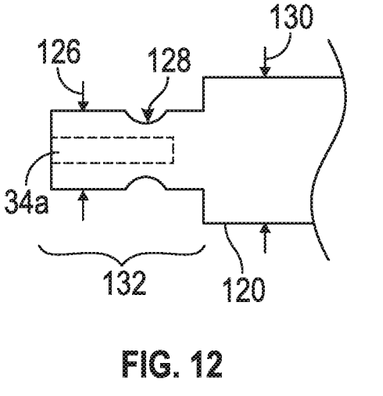

FIGS. 10-12 illustrate portions of various orthopedic devices 120 that can be used with the orthopedic device holder 2 (as shown in FIG. 2), as constructed in accordance with at least one example. Examples of orthopedic devices 120 include, but are not limited to, femoral or tibial intramedullary drills, headless pin drivers, hex screw drivers, reamers, tibial intramedullary rods, femoral intramedullary rods, among others. The orthopedic devices 120 can each include an engagement portion 132 that is inserted into the bores of the orthopedic device holder 2 (e.g., bore 10 or bore 28 as shown in FIG. 1). As shown in FIGS. 10-12, the engagement portion 132 includes a circumferential groove 128 that is configured to receive a portion of one or more locking balls (e.g., locking balls 94 or locking balls 74). The diameter 126 of the engagement portion 132 can be substantially the same or vary from the diameter 130 of the remaining portion of the orthopedic device 120. As illustrated in FIG. 10, diameter 130 is substantially the same as diameter 126. As illustrated in FIG. 11, diameter 130 is greater than the diameter 126. As illustrated in FIG. 12, diameter 130 is less than the diameter 126. However, regardless of the diameter 130, the orthopedic device 120 can be coupled to the orthopedic device holder 2 (as shown in FIG. 1).

VARIOUS NOTES

The above Detailed Description includes references to the accompanying drawings, which form a part of the Detailed Description. The drawings show, by way of illustration, specific embodiments in which the present catheter orthopedic device holder, kit, and method can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the inventive subject matter should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the terms "proximal" and "distal" are used to refer to a device holder element location relative to a caregiver user. For example, a proximal element portion is a portion closer to the user of the device holder, whereas a distal element portion is a portion farther away from the user of the device holder, such as the portions interacting with a patient recipient. In this document, the term "patient" is intended to include mammals, such as for human applications or veterinary applications.

In the appended claims, the terms "including" and "in which" are used as the plain-English equivalents of the respective terms "comprising" and "wherein." Also, in the following claims, the terms "including" and "comprising" are open-ended, that is, an assembly, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An orthopedic device holder, comprising:
   a handle having a proximal end, a distal end, and a longitudinal extent with a longitudinal axis between the proximal end and the distal end, the handle defining a channel with an opening at the distal end and a first bore in the longitudinal extent, wherein the first bore is perpendicular to the longitudinal axis;
   a plunger portion extending into the channel defining a second bore, wherein the second bore and first bore have identically shaped cross-sectional geometries with respect to one another such that both the second bore and the first bore are configured to interchangeably receive a portion of an orthopedic device; and
   a locking lever operably coupled to the handle and configured to move between a first position and a second position to simultaneously facilitate connection or release of the orthopedic device from either the first bore or the second bore.

2. The orthopedic device holder of claim 1, further comprising:
   a first locking mechanism operably coupled to the handle and moveable within a slot of the plunger portion between a first position and a second position, such that in the first position, the first locking mechanism is in a locked configuration with respect to the first bore and in the second position, the first locking mechanism is in an unlocked configuration with respect to the first bore; and
   a second locking mechanism mounted on the plunger portion and moveable between a first position and a second position, such that in the first position, the second locking mechanism is in a locked configuration with respect to the second bore, and in the second position, the second locking mechanism is in an unlocked configuration with respect to the second bore.

3. The orthopedic device holder of claim 2, wherein the second locking mechanism includes at least one locking ball, the at least one locking ball, when the second locking mechanism is in the first position, configured to extend at least partially through at least one opening in the plunger portion and into a mating recess of the orthopedic device.

4. The orthopedic device holder of claim 3, wherein the second locking mechanism, when in the first position, is configured to provide rotational constraint and axial constraint of the orthopedic device.

5. The orthopedic device holder of claim 1, wherein the first bore and the second bore both have a tri-lobe cross-sectional shape, including three flat surfaces.

6. The orthopedic device holder of claim 5, wherein for the second bore, the three flat surfaces are positioned equidistant from each other, each of the three flat surfaces is configured to engage with a corresponding one of three flat surfaces of the orthopedic device.

7. The orthopedic device holder of claim 5, further comprising at least one opening extending into an interior of the first bore that extends through one of the flat surfaces of the first bore.

8. The orthopedic device holder of claim 5, further comprising at least one opening extending into an interior of the second bore that extends through one of the flat surfaces of the second bore.

9. The orthopedic device holder of claim 1, wherein the first bore is perpendicular to the second bore.

10. An orthopedic device holder, comprising:
    a handle having a proximal end, a distal end, and a longitudinal extent with a longitudinal axis between the proximal end and the distal end, the handle defining a channel with an opening at the distal end and a first bore in the longitudinal extent, wherein the first bore is perpendicular to the channel;
    a plunger portion extending into the channel defining a second bore, wherein the second bore and first bore have identically shaped cross-sectional geometries with respect to one another such that both the second bore and the first bore are configured to interchangeably receive a portion of an orthopedic device;
    a first locking mechanism operably coupled to the handle and moveable within a slot of the plunger portion between a first position and a second position, such that in the first position, the first locking mechanism is in a locked configuration with respect to the first bore and in the second position, the first locking mechanism is in an unlocked configuration with respect to the first bore; and
    a second locking mechanism mounted on the plunger portion and moveable between a first position and a second position, such that in the first position, the second locking mechanism is in a locked configuration with respect to the second bore, and in the second position, the second locking mechanism is in an unlocked configuration with respect to the second bore.

11. The orthopedic device holder of claim 10, further comprising a locking lever operably coupled to the handle and configured to move between a first position and a second position to simultaneously move the second locking mechanism and the first locking mechanism from the respective first positions to the respective second positions to connect and release the orthopedic device from either the first bore or the second bore.

12. The orthopedic device holder of claim 10, wherein the first bore is perpendicular to the longitudinal axis.

13. An orthopedic device holder, comprising:
a handle having a distal end and a proximal end and a longitudinal extent with a longitudinal axis between the distal end and the proximal end thereof, wherein the handle has a first aperture in the longitudinal extent with a first tri-lobe connection feature and a second aperture in the distal end;
a second tri-lobe connection feature mounted in the second aperture, wherein the first tri-lobe connection has an identical shaped cross-sectional geometry as the second tri-lobe connection feature such that either can interchangeably receive the one or more orthopedic devices; and
a locking lever operably coupled to the handle and configured to move between a. first position and a second position to simultaneously facilitate connection or release of one of the one or more orthopedic devices from either the first aperture or the second aperture.

14. The orthopedic device holder of claim 13, wherein the first aperture is perpendicular to the longitudinal axis.

15. The orthopedic device holder of claim 13, wherein the first aperture is perpendicular to the second aperture.

16. The orthopedic device holder of claim 13, wherein the first aperture comprises a first bore and further comprising:
a plunger portion extending into the second aperture and defining a second bore;
a first locking mechanism operably coupled to the handle and moveable within a slot of the plunger portion between a first position and a second position, such that in the first position, the first locking mechanism is in a locked configuration with respect to the first bore and in the second position, the first locking mechanism is in an unlocked configuration with respect to the first bore; and
a second locking mechanism mounted on the plunger portion and moveable between a first position and a second position, such that in the first position, the second locking mechanism is in a locked configuration with respect to the second bore, and in the second position, the second locking mechanism is in an unlocked configuration with respect to the second bore.

17. The orthopedic system of claim 16, wherein for both the first bore and the second bore, three flat surfaces are positioned equidistant from each other, each of the three flat surfaces is configured to engage with a corresponding one of three flat surfaces of the orthopedic device.

* * * * *

UNITED STATES PATENT AND TRADEMARK OFFICE
CERTIFICATE OF CORRECTION

| | | |
|---|---|---|
| PATENT NO. | : 11,331,134 B2 | |
| APPLICATION NO. | : 16/297898 | |
| DATED | : May 17, 2022 | |
| INVENTOR(S) | : Jones et al. | |

It is certified that error appears in the above-identified patent and that said Letters Patent is hereby corrected as shown below:

In the Claims

In Column 13, Line 18, in Claim 13, delete "a." and insert --a-- therefor

Signed and Sealed this
Fifth Day of July, 2022

Katherine Kelly Vidal
*Director of the United States Patent and Trademark Office*